(12) United States Patent
Ashrafuzzaman et al.

(10) Patent No.: US 9,529,006 B1
(45) Date of Patent: Dec. 27, 2016

(54) METHOD FOR DIRECT DETECTION OF LIPID BINDING AGENTS IN MEMBRANE

(71) Applicant: KING SAUD UNIVERSITY, Riyadh (SA)

(72) Inventors: Md. Ashrafuzzaman, Riyadh (SA); Chih-Yuan Tseng, Edmonton (CA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/882,352

(22) Filed: Oct. 13, 2015

(51) Int. Cl.
*G01N 33/92* (2006.01)
*G01N 33/50* (2006.01)

(52) U.S. Cl.
CPC .......... *G01N 33/92* (2013.01); *G01N 33/5014* (2013.01)

(58) Field of Classification Search
CPC ............................ G01N 33/92; G01N 33/5014
USPC ................................ 435/6.1, 6.17, 7.1, 287.1
See application file for complete search history.

(56) References Cited

U.S. PATENT DOCUMENTS 8,484,010 B2 7/2013 Tuszynski et al.
2006/0014013 A1* 1/2006 Saavedra ................ A61L 27/34
428/338

OTHER PUBLICATIONS

Frantescu et al. Biochemistry, vol. 68, Issue 2, May 2006, pp. 158-170.*
Charych et al. Science, vol. 261, Jul. 1993, pp. 585-588.*
Chih-Yuan Tseng et al., "Using Entropy Leads to Better Understanding of Biological Systems", Entropy (2010), vol. 2, pp. 2450-2469.
Md. Ashrafuzzaman, "Aptamers as Both Drugs and Drug-Carriers", Biomed Research International, Hindawi Publishing Corporation, vol. 2014, Article 607923, pp. 1-21 (2014).

* cited by examiner

*Primary Examiner* — Janet Epps-Smith
(74) *Attorney, Agent, or Firm* — Richard C. Litman

(57) ABSTRACT

The method for direct detection of lipid binding agents in membrane includes dissolving a lipid in an organic solvent in a container; evaporating off the organic solvent to create a lipid film on the inside wall of the container; adding a buffer solution; adding a known volume of a membrane active agent to the buffer solution; incubating the solution in the dark for a period of time; removing the buffer solution from the container to provide a solution of sample A; washing the container with a buffer solution; adding an organic solvent while stirring the container to dissolve the lipid film to create a homogenous solution B; and measuring the absorbance of the samples A and B by absorption spectroscopy. The method may further include developing a universal probability function to test and quantify a membrane-based cytotoxicity of general drug candidates.

10 Claims, 9 Drawing Sheets

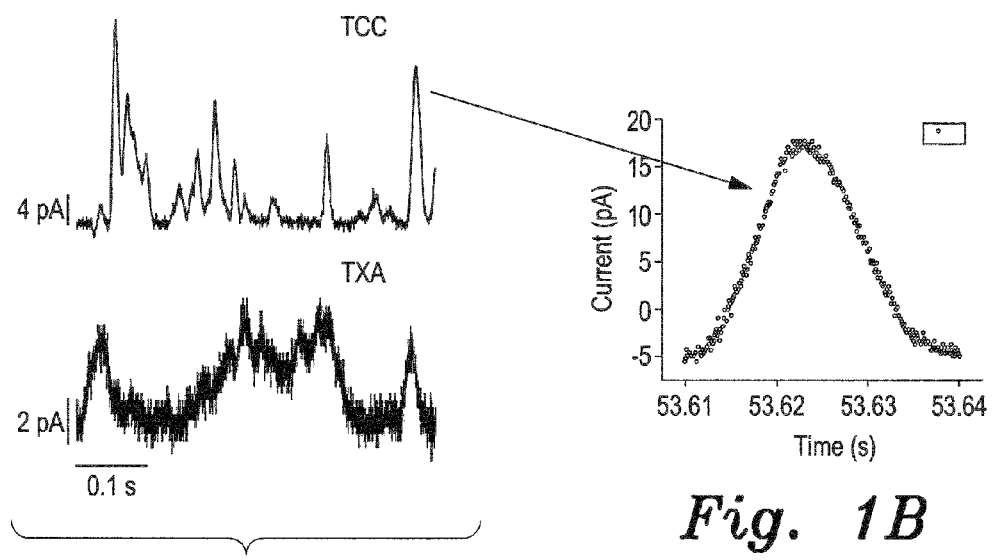
Fig. 1A
Fig. 1B
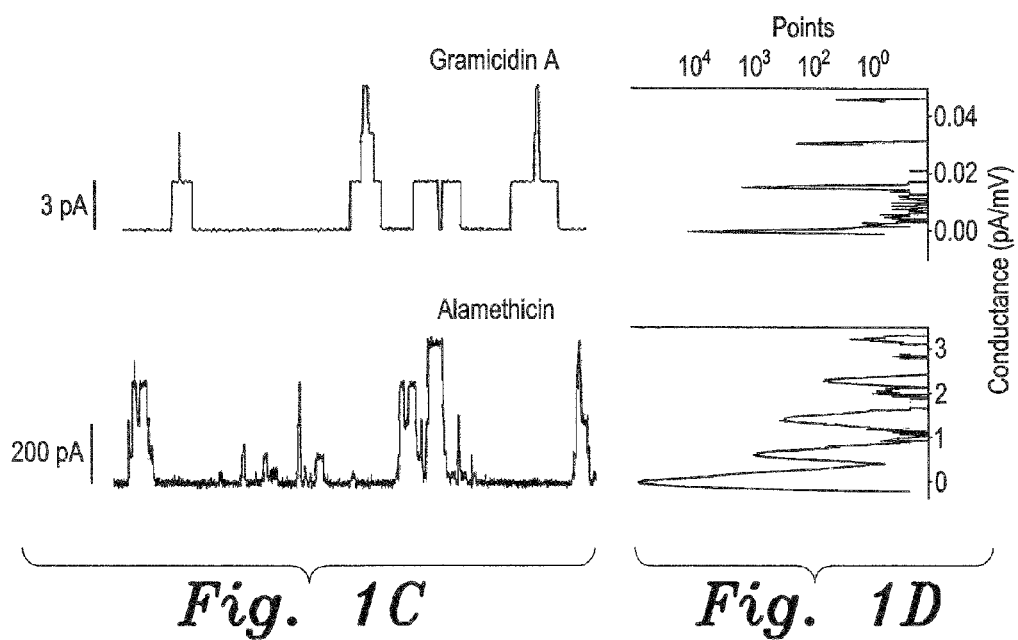
Fig. 1C
Fig. 1D

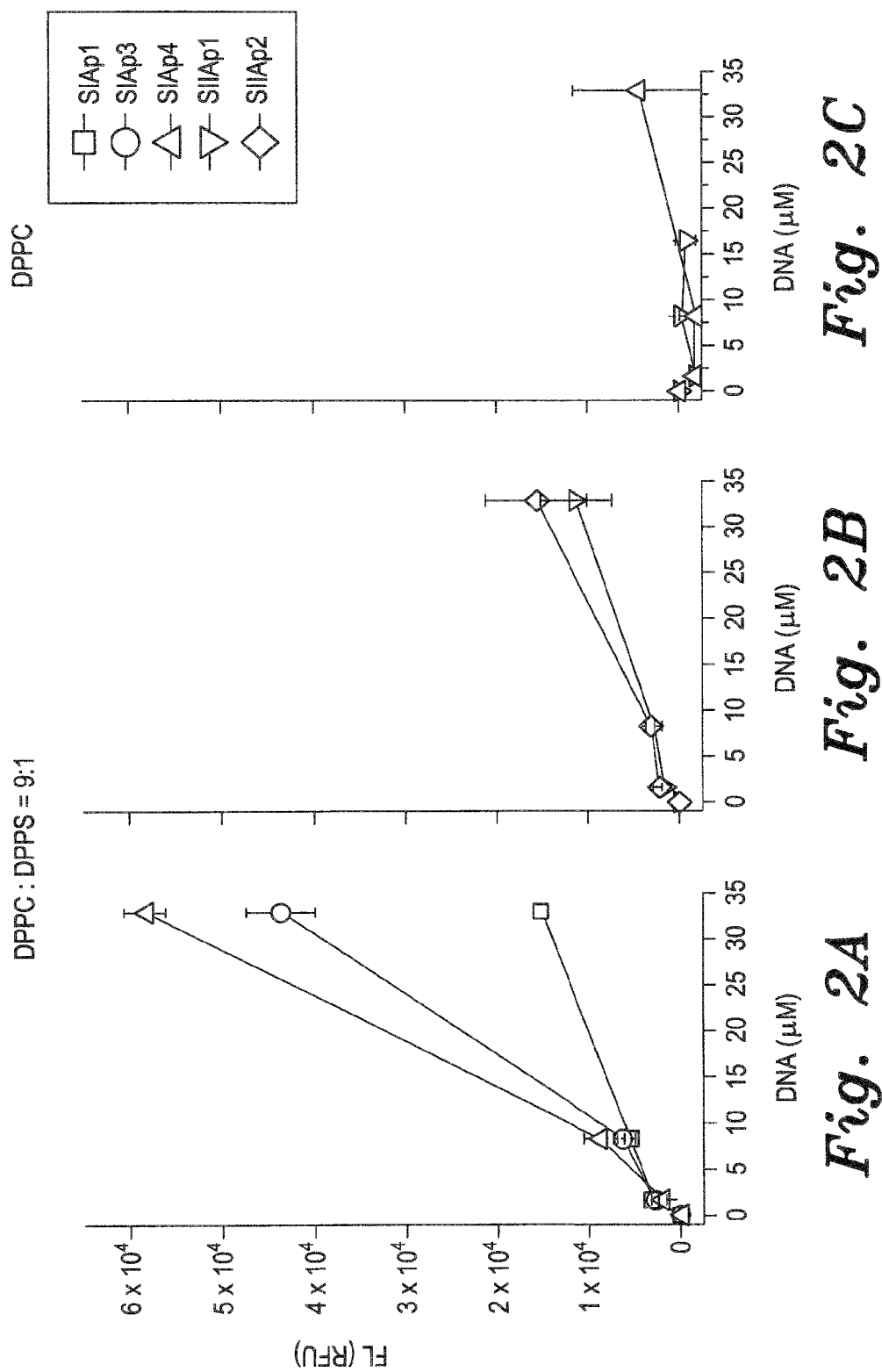

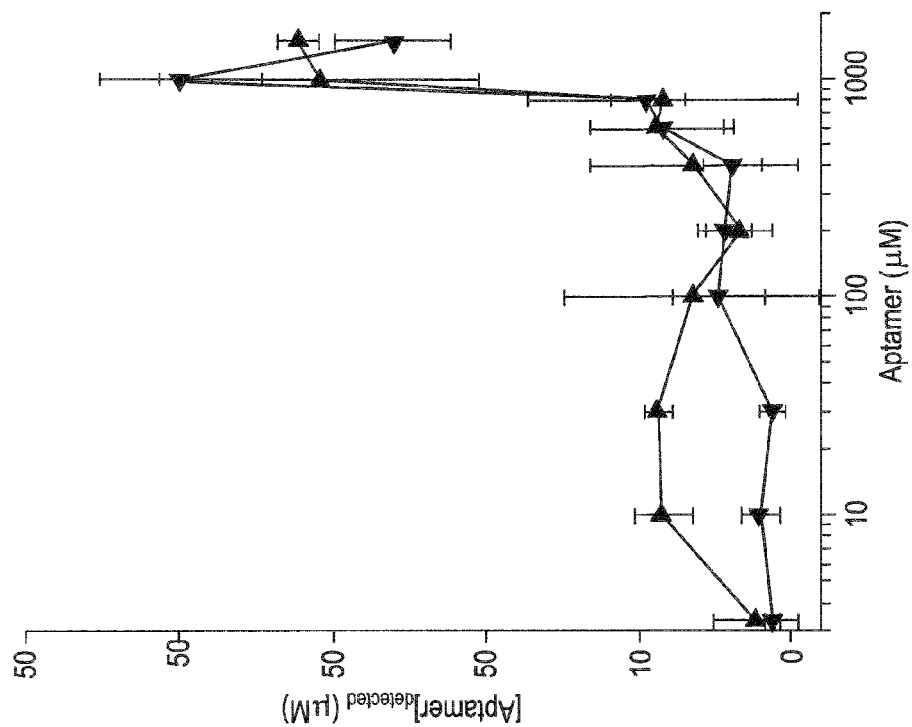
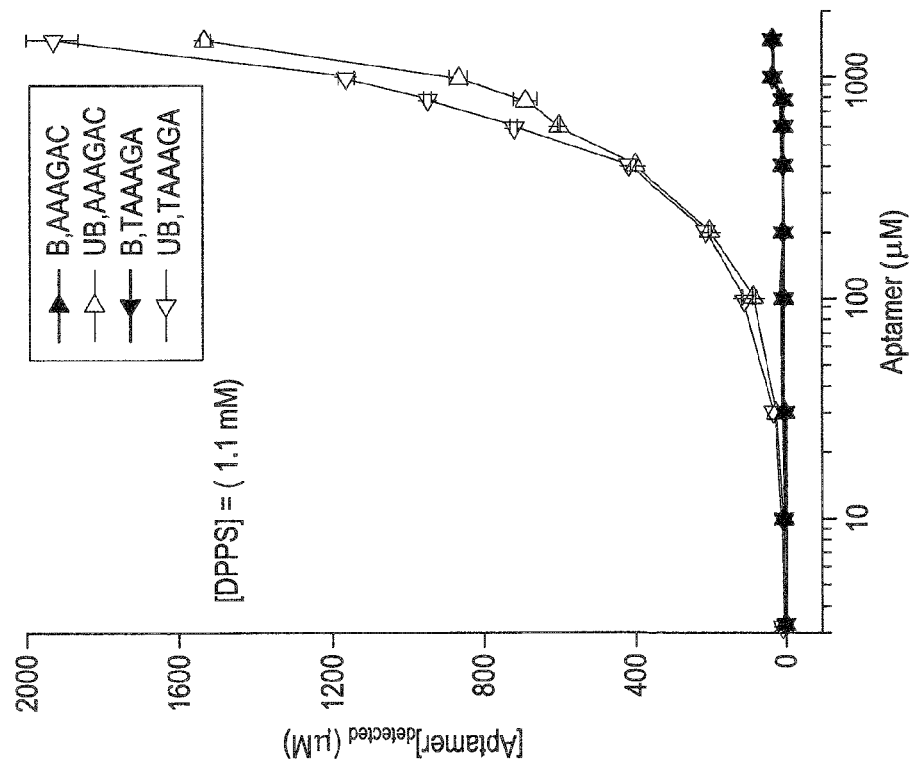
Fig. 4A
Fig. 4B

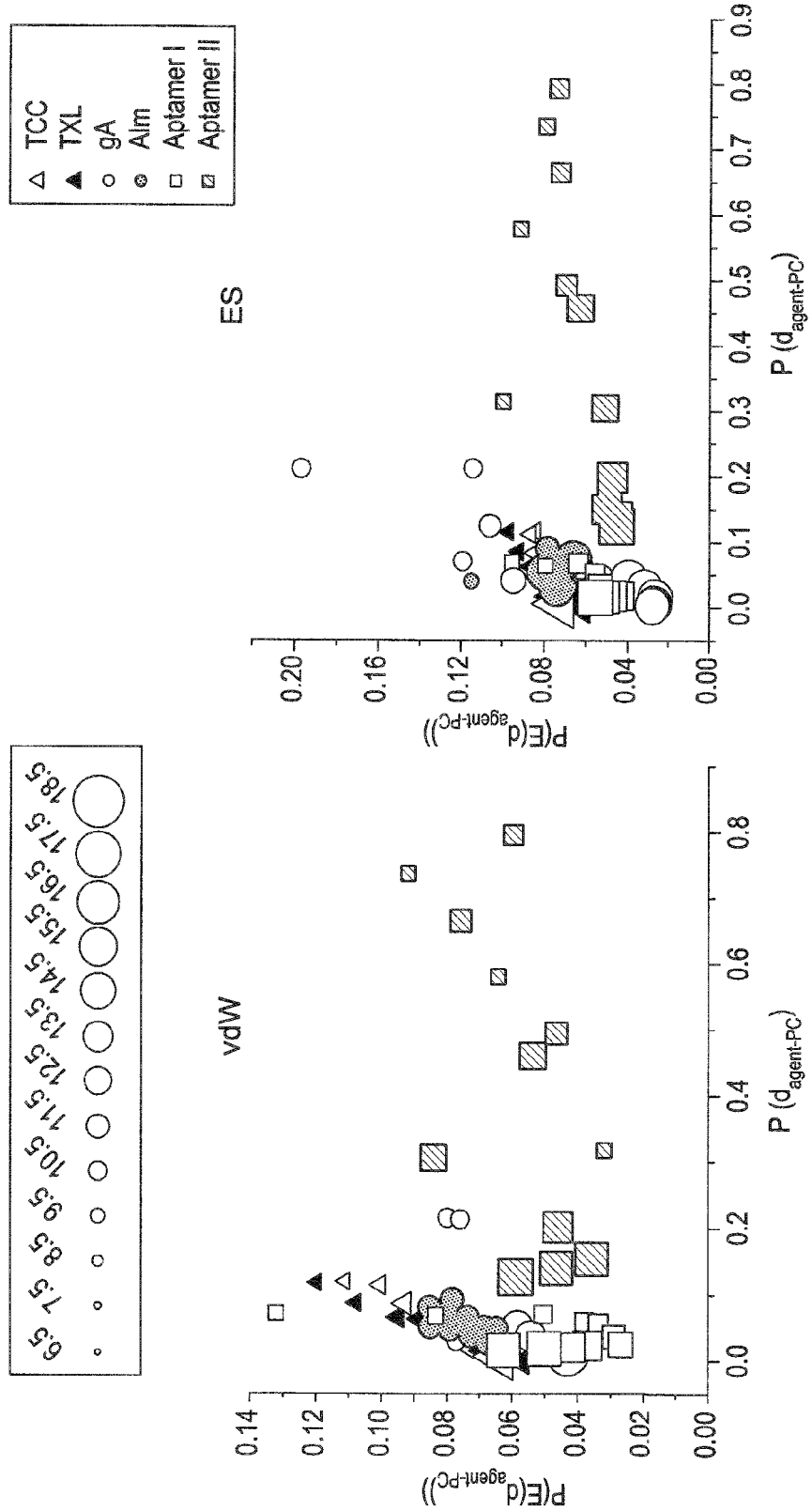

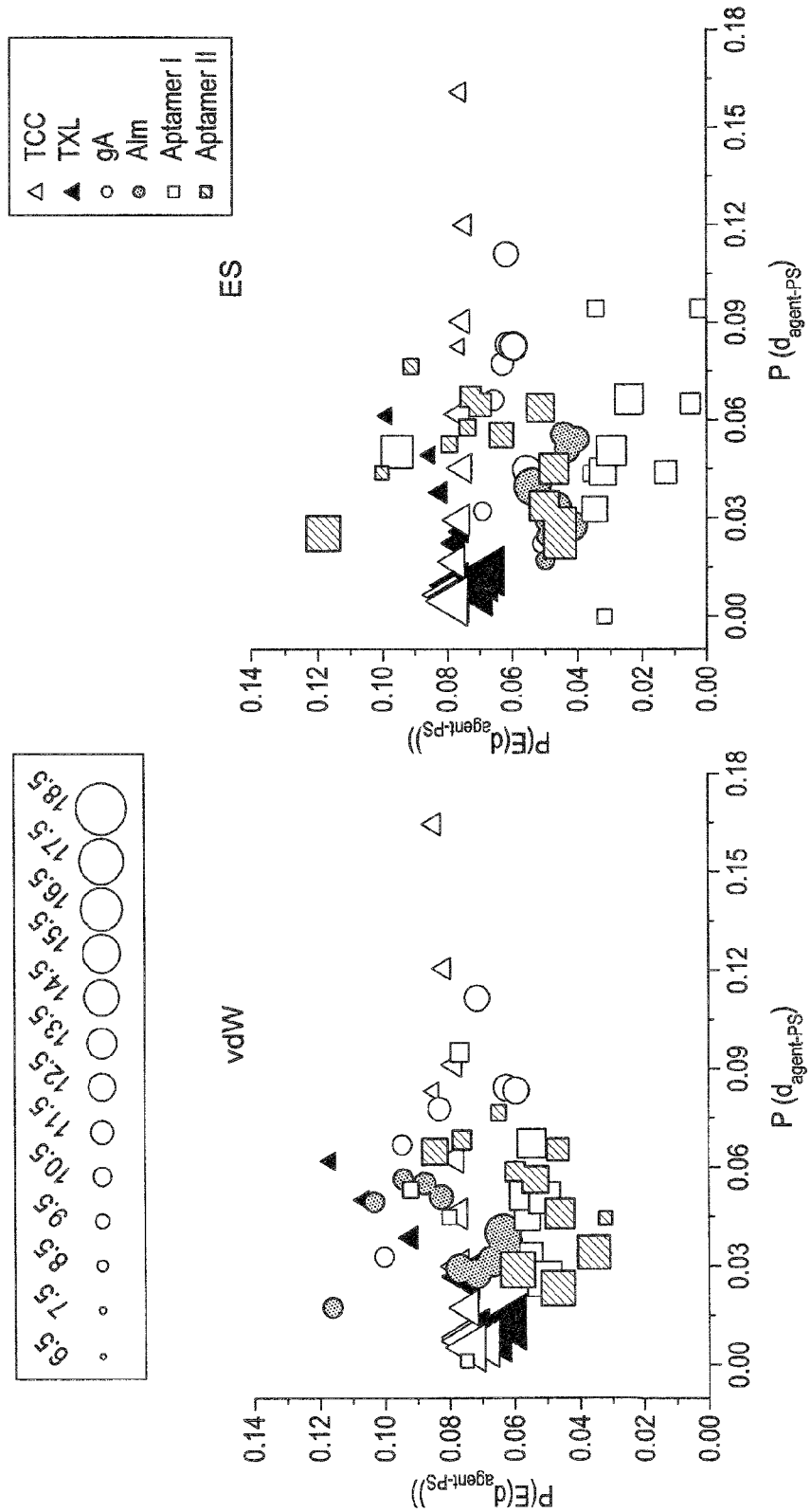

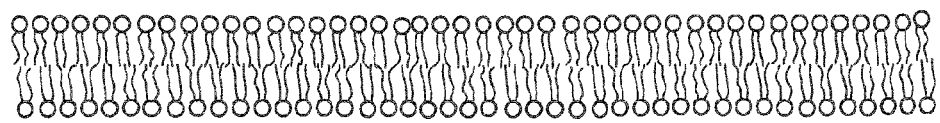
*Fig. 8A*
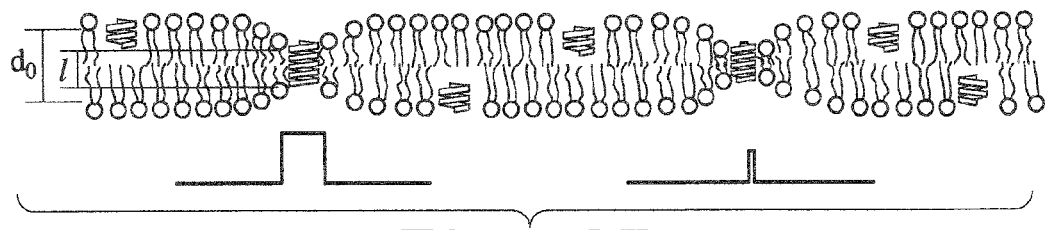
*Fig. 8B*
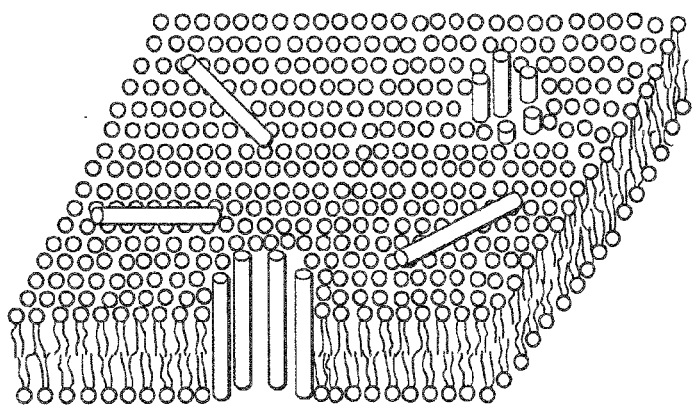
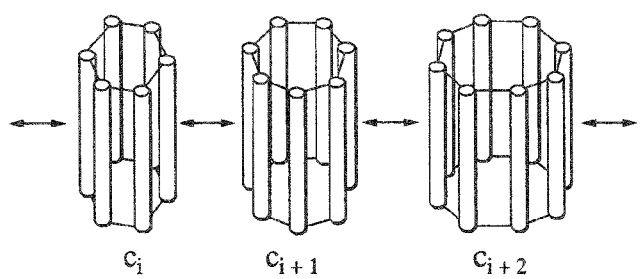
*Fig. 8C*

METHOD FOR DIRECT DETECTION OF LIPID BINDING AGENTS IN MEMBRANE

INCORPORATION BY REFERENCE OF MATERIAL SUBMITTED IN A COMPUTER READABLE FORM

The applicants hereby incorporate by reference the sequence listing contained in the ASCII text file titled 32693.37_Sequence_Listing_Aptamers_ST25.txt, created on 11/12/15 and having 1 KB of data.

BACKGROUND OF THE INVENTION

1. Field of the Invention

The present invention relates to a bio-assay method, and particularly to a method for direct detection of lipid binding agents in membrane to quantitatively detect cell membrane active agents (MAAs) directly in lipid membranes.

2. Description of the Related Art

Membrane proteins (MPs) in a cell represent about 1% of the cellular proteins, but 50% of the cellular constituent targeted drugs end up acting on MPs. Whenever membrane is approached by agents, some of which physically reside in the vicinity (e.g., MPs), while others get dragged from external sources (e.g., drugs), the membrane's main constituent lipids experience a state of physical coexistence with the agents. The agents are found to perform various physiological activities due to their membrane-bound coexistence. Based on their specific or nonspecific actions upon membrane, we define them as a class or various classes of membrane active agents (MAAs). Theoretical, computational, and experimental techniques may be used to understand the membrane-targeted activities through investigating complex structures resulting from MAA-lipid coexistences. The lipid bilayer hosted ion channels due to MAAs, e.g., MPs or antimicrobial peptides (AMPs), are examples of theoretically understandable and experimentally detectable events. The MAA-induced events, and occasionally lipid reorganization, also creates specific stable channel structures in the membranes. For example, ceramide is found to induce lipid channels.

The geometry of cluster structure also is found to be MAA specific. In recent investigations, small DNA oligos that are called 'aptamers' are found to show physical lipid-specific liposome binding properties, and thus perhaps appear with properties that make them includable in the class of MAAs.

Use of membrane active agents (MAAs), such as peptides, aptamers, general biomolecules, small proteins, detergents, etc., is a common practice among scientists for various purposes, such as structure analysis, disease research, drug discovery research, etc. Also, the structural aspects of MAA-lipid complexes, along with their phenomenological statistics and dynamics, are quite known. However, quantitative analysis to pinpoint mole fraction binding of MAAs with membrane, the energetics behind binding, and molecular mechanisms to determine the quantitative binding probability are either not available or limited, to date. Besides, the underlying molecular mechanisms are left either unexplored or addressed poorly using apparently a few incorrect hypotheses, approaches, and formalisms. Therefore, it would be desirable to develop a direct detection method (DDM) to detect cell membrane active agents (MAAs) quantitatively directly in lipid membrane and thereby develop a method that could act as a 'universal platform' to test and certify an agent as a candidate with measurable probability of interaction or binding with a target structure in a biological system.

Thus, a method for direct detection of lipid binding agents in membrane solving the aforementioned problems is desired.

SUMMARY OF THE INVENTION

The method for direct detection of lipid binding agents in membrane includes dissolving a lipid in an organic solvent in a container; evaporating the organic solvent to create a lipid film on the inside wall of the container; adding a buffer solution; adding a known volume of a membrane active agent to the buffer solution; incubating the solution in the dark for a period of time; removing the buffer solution from the container to provide a solution of sample A; washing the container with a buffer solution; adding an organic solvent to the container while stirring to dissolve the lipid film and create a homogenous solution B; and measuring the absorbance of the samples A and B by absorption spectroscopy. A method for detecting an interaction between a membrane active agent and a lipid can further include developing a universal probability function to test and certify an agent as a candidate with measurable probability of interaction or binding with a target structure in a biological system, and further include quantifying a membrane-based cytotoxicity of general drug candidates.

These and other features of the present invention will become readily apparent upon further review of the following specification and drawings.

BRIEF DESCRIPTION OF THE DRAWINGS

FIG. 1A is electrophysiological recordings of lipid bilayer membranes doped with thiocolchicoside (TCC) and taxol (TXL), respectively.

FIG. 1B is a high resolution electrophysiological recording of the rightmost peak of the TCC trace in FIG. 1A.

FIG. 1C is an electrophysiological recording showing the rectangular-shaped conductance events of the antimicrobial peptides gramicidin A (gA) and alamethicin (Alm) in gA and Alm membrane channels.

FIG. 1D are point count plots of the current traces of FIG. 1C through gA channels and Alm channels, respectively, showing peaks at discrete values of conductance.

FIGS. 2A, 2B, and 2C are graphs of the binding affinity and selectivity of designed DNA aptamers.

FIG. 4A is a plot showing fluorescence spectroscopy detection of liposome binding of two aptamers (AAAGAC and TAAAGA), both bound and unbound.

FIG. 4B is an expanded view of a portion of the plot of FIG. 4A for the bound aptamers.

FIGS. 5A, 5B, 5C, and 5D show the analysis of Molecular Dynamic (MD) results of all lipid-agent pairs.

FIGS. 8A, 8B, 8C, and 8D depict how the membrane active agents perturb bilayers and alter their shapes.

Similar reference characters denote corresponding features consistently throughout the attached drawings.

DETAILED DESCRIPTION OF THE PREFERRED EMBODIMENTS

Figures 3A, 3B:
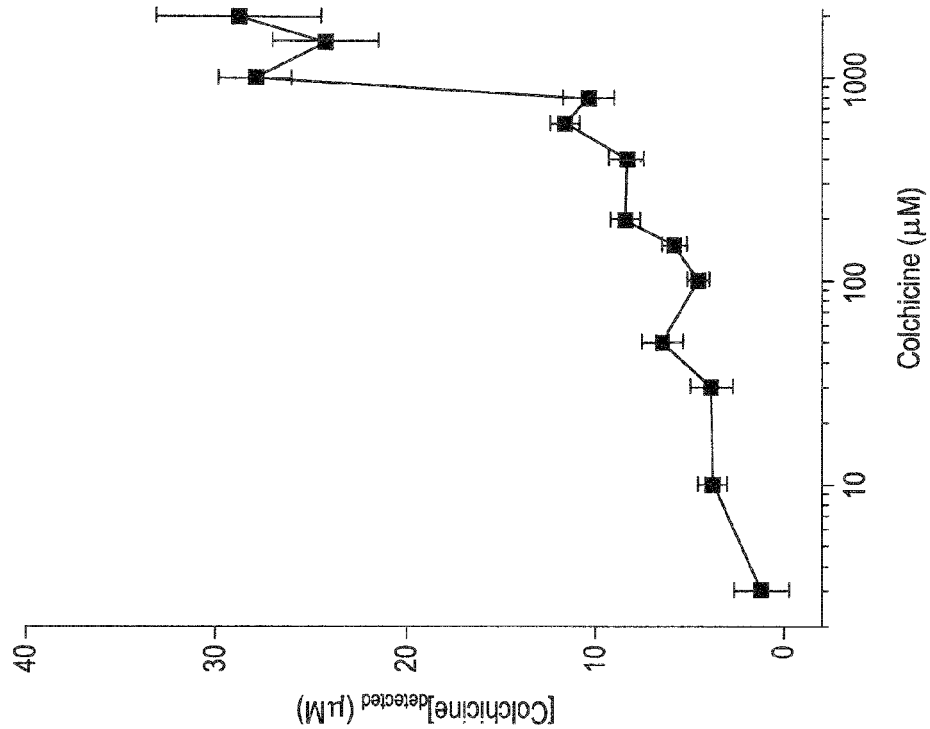
FIG. 3A is a plot showing the Colchicine-DOPC (Dioleoylphosphatidylcholine) liposome assay for bound (B) and unbound (UB) colchicine using absorbance spectroscopy.
FIG. 3B is an expanded view of a portion of the plot of FIG. 3A for unbound colchicine.

The method for direct detection of lipid binding agents in membrane in in vitro biological systems uses absorbance spectroscopy. The method directly detects the molecules and quantifies the membrane-bound molecules (B) relative to the unbound ones (UB) to model and develop a universal probability function to test and certify an agent as a candidate with measurable probability of interaction or binding with a target structure in a biological system. The method can further comprise quantifying a membrane-based cytotoxicity of general drug candidates in cell membrane during targeted drug discovery.

The method for direct detection of lipid binding agents in membrane comprises dissolving a lipid in an organic solvent in a container; evaporating off the organic solvent to create a lipid film on the inside wall of said container; adding a buffer solution; adding a known volume of a membrane active agent to the buffer solution; incubating the solution in the dark for a period of time; removing the buffer solution from the container to provide a solution of sample A; washing the container with a buffer solution; adding an organic solvent while stirring the container to dissolve the lipid film to create a homogenous solution B; and measuring the absorbance of the samples A and B by absorption spectroscopy. The method can further comprise quantifying the lipid binding energies by the membrane active agents from the absorbance measurement. Typically, the organic solvent used is methanol and the container is typically an Eppendorf tube. Typically, the membrane active agent is colchicine or an aptamer selected from the group consisting of aptamers 5'-AAAAGA-3',5'-AAAGAC-3' or combinations thereof. The lipid is generally selected from the group consisting of phosphatidylcholine (PC), phosphatidylserine (PS) and Dioleoylphosphatidylcholine (DOPC). In other embodiments, the lipid can be a liposome.

The method can further comprise developing a universal probability function to test and certify an agent as a candidate with measurable probability of interaction or binding with a target structure in a biological system. The method can further comprise quantifying a membrane-based cytotoxicity of general drug candidates during drug discovery.

As defined herein, a liposome is a spherical vesicle having at least one lipid bilayer. The liposome can be used as a vehicle for administration of nutrients and pharmaceutical drugs. Liposomes can be prepared routinely by disrupting biological membranes (such as by sonication). Two different kinds of processes to address membrane effects of all three different classes of MAAs were developed. First, the electrophysiology (EP) trials were performed to record membrane currents across lipid bilayer membranes doped with AMPs (antimicrobial peptides) or CDs (chemotherapy drugs). This technique helps to detect the presence of any stable, semi-stable or transient structures that might be induced into the lipid bilayer membrane as a result of MAA-lipid coexistence. To understand the membrane effect of aptamers, fluorescence (FL) measurements on liposome bound aptamers were performed. This method helps to understand the general lipid membrane binding of aptamers.

The membrane effects of AMPs were tested using established electrophysiology technique. Here, gA (gramicidin A) monomer with 15 amino acids was used for constructing gA channels and Alm (alamethicin) monomers were used for constructing Alm channels in a bilayer constructed using lipid 1,2-Dioleoyl-sn-Glycero-3-Phosphocholine. For the membrane effects of CDs, planar lipid bilayers were formed by applying a lipid cocktail of Phosphoethanolamine: phosphatydyleserine: phosphatidylcholine (5:3:2, v/v/v)/n-decane using the painting method over a 150 μm septum of a bilayer cuvette. The aptamer-lipid binding aspects were addressed by preparing liposomes using liposome technology. The liposomes were prepared with 1,2-dipalmitoyl-sn-glycero-3-phosphatidylcholine (DPPC) and 1,2-dipalmitoyl-sn-glycero-3-phospho-L-serine (sodium salt) (DPPS). Buffer with the liposome-bound and unbound aptamers containing 6-carboxyfluorescein (6-FAM) fluorescent tag attached at the 3' end of the DNA sequence was separated using standard binding assay. The solution with bound aptamers was then investigated for fluorescence quantification. The following examples will further illustrate the direct detection method (DDM).

Example 1

Preparation of Planar Lipid bilayers

For the membrane effects of chemotherapy drugs (CDs) (e.g. TCC thiocolchicoside and TXL taxol, planar lipid bilayers were formed by applying a lipid cocktail of phosphoethanolamine: phosphatydyleserine: phosphatidylcholine (5:3:2, v/v/v)/n-decane using the painting method over a 150 μm septum of a bilayer cuvette according to known literature methods.

Example 2

Preparation of Liposomes

The aptamer-lipid binding aspects were addressed by preparing liposomes using known liposome technology. The liposomes were prepared with, 1,2-dipalmitoyl-sn-glycero-3-phosphatidylcholine (DPPC) and 1,2-dipalmitoyl-sn-glycero-3-phospho-L-serine (sodium salt) (DPPS). Buffer with the liposome bound and unbound aptamers containing 6-carboxyfluorescein (6-FAM) fluorescent tag attached at the 3' end of the DNA sequence was separated using standard binding assay. The solution with bound aptamers was then investigated for fluorescence quantification.

Example 3

Membrane Currents Across Lipid Bilayers

Membrane currents across lipid bilayer membranes doped with antimicrobial peptides (AMPs) or chemotherapy drugs (CDs) were investigated. The pattern of the general time dependent ion pore conducting current fluctuations is MAA specific. The amplitude and stability of the current events are found to vary due to the differences in the structures of MAAs. Some ion pores conduct currents with constant amplitudes over a period of time considered as pore lifetime. While a few other pores are found to conduct currents with fluctuating amplitudes over their lifetimes.

FIGS. 1A-1D display the conductance events induced by thiocolchicoside (TCC) and taxol (TXL). FIG. 1A shows the triangular-shaped conductance events induced by TCC and TXL, both at 90 µM, pH=5.7, V=100 mV. Both traces were filtered at 20 kHz but the lower trace shows higher noise due to its presentation (current axis) at an amplified scale. FIG. 1B shows a high resolution plot (shown in the right side of the arrow) of a single event only showing individual points (in origin 8.5 plot). FIG. 1C shows the rectangular-shape conductance events in gramicidin A (gA) and alamethicin (Alm) channels. The gA channel activity was recorded at V=200 mV and Alm at V=150 mV. Here IgA=29±2, 113±5, 243±9 and 386±10 pA respectively are the discrete current levels 0, 1, 2, 3, . . . , etc. in Alm channel. Traces representing gA and Alm channel activities in phospholipid bilayers were recorded at filter frequencies 2 kHz and 20 kHz, respectively. A lower filter frequency for traces representing gA channel activity is alright because of the channel's relatively higher stability. In (B) the point count plots of the current traces through gA and Alm channels peak at discrete values of conductance.

AMP gA is reported to induce conductance events that conducts constant current $I_{gA}$ pA over its lifetime $\tau_{gA}$. At the formation and breaking of a gA channel the current undergoes transitions between $0 \to I_{gA}$ pA and $I_{gA} \to 0$ pA respectively. The current transitions between $0 \leftrightarrow I_{gA}$ pA happen instantaneously that means current transitions take almost no time. Here, $I_{gA}$ is constant (~in low range pA) for any gA channel but $T_O$ appears with all possible values within a range 0 to a very high value in ms order]. With varied number of amino acids in gA monomer the value of both $I_{gA}$ and $\tau_{gA}$ vary. Detailed analysis can be found in ref. [2-6]. Likewise, in case of Alm channel formation/breaking the current transitions between $0 \leftrightarrow I_{Alm}^i$ pA happen instantaneously. Here $I_{Alm}^i$ is the current conducted by i-th conductance state of an Alm channel. Correspondingly, $I_{Alm}^0$, $I_{Alm}^1$, $I_{Alm}^2$, . . . , etc. are the values for the discrete current levels 0, 1, 2, . . . , etc. In Alm channels back-and-forth instantaneous current transitions between discrete current levels i and j that is between currents $I_{Alm}^i$ and $I_{Alm}^j$ also happen. Here j=0, 1, 2, . . . , etc. with j≠i. The order of the values of $I_{Alm}^i$ is found in FIG. 1. The point count plot for gA and Alm channel record shows peaks at discrete conductance values at $N_{gA} \cdot I_{gA}/V$ for gA channel with $N_{gA}$=1, 2, 3, . . . etc. is the number of gA channels detected at the same time or $I_{Alm}^i/V$ for Alm channel. Peak at 0.0 pA/mV stands for baseline. The trend of decreasing peak areas with increasing discrete conductance values suggests that membrane conductance mostly originates from single events for gA channels or smaller channel conductance states for Alm channels.

CDs TCC and TXL are both found to induce conductance events that conduct time dependent currents $I_{CD}$ (t). Importantly, $I_{CD}$ (t) varies spontaneously between various values over a period of time. The main difference between AMP-induced and CD-induced membrane current levels is that in the former case the current transitions happen instantaneously while in the latter case the current transition is time dependent. That is why, the former ones appear with rectangular type current levels (with back-and-forth fluctuations for the case of Alm's) over the duration of channel stability while the latter ones appear with novel triangular type current levels. Although the former ones show stable current level with non-zero current values the latter ones show no such stability in the current level rather it fluctuates with time.

Figure 8D:
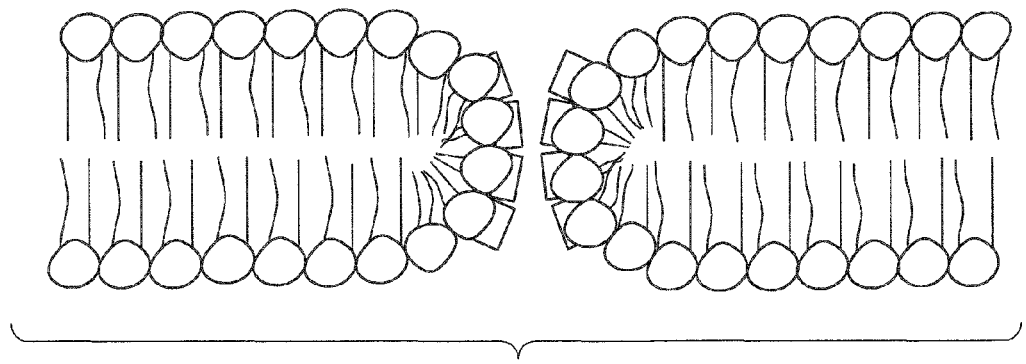

The characteristics of current levels are found to be MAA specific and vary for different classes of MAAs. The MAA specificity means perhaps the MAA specific structures of MAA-lipid complexes induced inside lipid bilayer membranes as mentioned earlier, e.g. as shown in FIG. 8.

The comparable membrane current traces as presented in FIG. 1 clearly suggests that both AMPs and CDs induce conductance events across lipid bilayer membranes. CD induced pores are predicted to be lipid-lined toroidal type with a spontaneously varying constant conductance of the pore in contrast to the protein lined channels reported due to the effects of AMPs gA and Alm where the channel conductance remains unchanged during the lifetime of the specific conductance state of the channels. Despite having varied molecular structures members of both classes of AMPs and CDs are found to induce ion pores/channels across lipid membranes but of course with various types of MAA specific current levels or conductance phenomena. The other class of small DNA oligos 'aptamers' appear as MAAs by showing substantial lipid and aptamer specific liposome binding. All members of these three classes of MAAs namely AMPs, CDs and aptamers are found to be membrane active in different ways.

Example 4

Fluorescence Measurements on Liposome Bound Aptamers

Binding affinity and selectivity of designed DNA aptamers were measured. FIG. 2 shows both general and lipid specific liposome binding of aptamers. The fluorescence (FL) measured in relative fluorescence units (RFU) is plotted against the [DNA] aptamer concentration. FIG. 2A shows the selective binding of aptamer SIAp1, SIAp 3 and SIAp 4 with liposomes containing PS. FIG. 2B shows the selective binding of aptamer and SIIAp1 and SIIAp2 with liposomes containing PS. FIG. 2C shows the low non-specific binding of designed aptamer SIAp4 and SIIAp1 with liposome containing only PC. These aptamers are discovered primarily for their possible PS binding that would help detect induced apoptosis in cancerous cells.

TABLE 1

Two sets of DNA aptamers designed for lipid binding

| Name | Sequence (5' → 3') | PS | PC |
|---|---|---|---|
| SIAp1 | AAAAGA | 0.23 ± 0.11 | 0.06 ± 0.02 |
| SIAp2 | AAAGAG | N/A | N/A |
| SIAp 3 | TAAAGA | 0.57 ± 0.15 | 0.31 ± 0.15 |
| SIAp 4 | AAAGAC | 0.54 ± 0.19 | 0.41 ± 0.08 |
| SIIAp1 (SEQ ID NO: 1) | CAGAAAAAAAC | 0.4 ± 0.2 | 0.41 ± 0.14 |
| SIIAp2 (SEQ ID NO: 2) | CAGAAAAAAAT | 0.31 ± 0.12 | 0.29 ± 0.19 |

SI is designed based on total energy and SII is designed using interaction energy. The third and fourth column list probabilities of designed aptamers and phospholipid within $6 < d_{PS\text{-}lipid} < 16$ Å.

PS externalization is a cell membrane's normal phenomenon related to apoptosis. The liposome binding shows aptamer specificity that is the relative quantitative liposome binding depends on sequences and number of nucleotide bases in aptamers. Among the aptamers tested 2 are found to bind relatively stronger to liposomes containing 10% PS. Others show poor binding. Longer ones are generally poor liposome binding aptamers. All aptamers are generally found to show negligible binding with liposomes containing no PS. These fluorescence based experimental measurements clearly suggest for both lipid and aptamer (sequence and length) specificity in liposome binding of aptamers and that suggests for PS specific binding.

Example 5

Development of Direct Detection Method (DDM) to Quantify the MAAs in Membranes The membrane active agents (MAAs) used for the trials were two agents namely colchicine whose derivatives are confirmed to form ion pores and a few short candidate aptamers 5'-AAAAGA-3' (Aptamer I) and 5'-AAAGAC-3' (Aptamer II) and a long candidate that shows no liposome binding of PS binding aptamers, e.g., aptamers 5'-AAAAGA-3' (Aptamer I) and 5'-AAAGAC-3' (Aptamer II). The binding assay for a long aptamer is considered as a negative control that shows no PS binding from fluorescence studies. All aptamers are also tested for their possible absolute PC binding.

Initially, a candidate lipid powder or lipid film after evaporating chloroform is dissolved in methanol solution. A certain volume of this lipid solution is taken inside an Eppendorf tube or in a well of a 96 well plate to be considered here as 'incubation tube'. This lipid solution inside tube is kept under hood for overnight drying. In the following morning after the methanol gets evaporated, a lipid film gets created on the interior wall of the tube. The tube is then fixed in place and placed in a dark room without any vibrations. Then a certain volume of buffer is added inside the tube with a lipid film on its interior wall. The buffer volume should be covering the top most lipid traces in the lipid film. Usually if 90 µL of lipid from methanol stock is added in the tube for overnight drying then around the same or somewhat lower volume of experimental buffer should be added.

Thereafter, an aliquot from a concentrated experimental stock of membrane active agents (MAAs) is added. The final volume including buffer and aliquot of MAA stock altogether should be such that inside the tube the top most traces of lipid film sinks inside the buffer. Usually, to make an adjustment in the calculation if the final volume is made 100 µL (consider that as mentioned earlier 90 µL of lipid from methanol stock was used for drying) we find that the purpose is served nicely. The added MAA now ensures a concentration inside the incubation tube and this is now considered to be $C_{MAA}$.

To prepare a highly concentrated stock for an MAA, specific MAA dissolving solvent can be chosen selected from the group consisting of DMSO, methanol or any other specific MAA dissolving solvent. Certain volume of this master stock solution is taken and added into certain volume of the experimental buffer thereby finally creating an experimental stock in buffer to be used for experimental purposes. While performing high concentration MAA studies the original master stock can be used, in e.g., DMSO as long as the total volume of that added aliquot in DMSO does not exceed 1% of the experimental buffer to avoid effects of DMSO.

After having the aliquot of MAA stock added into the buffer covering the dried lipid film the tube is incubated in the dark for an hour and without any mechanical disturbance and far away from any kind of electrical fields. This is enough time and the condition is favorable for any possible interaction between MAA molecules and lipids of the vesicles created on the interior wall of the tube.

After 1 hour's incubation the whole buffer is gently suck (in this case mentioned 100 µL) from the incubation tube and collected it in a highly clean glass tube. Care must be taken to avoid touching the lipid sticking in the interior wall of the well with the tip of the sucking pipette. The incubation tube with the same volume (100 µL) of experimental buffer is washed two more times and collected in the same glass tube where the first collected buffer has been placed. This way only lipid bound MAAs is left inside incubation tube. This should now measure 3 times the incubation volume of the buffer that is in this case it is 300 µL. This glass tube contains all the MAAs that avoided binding with lipids or generally with vesicles. This sample is considered TB' ('UB' stands for unbound with lipids or vesicles). Next, 100 µL methanol is poured into the incubation tube and rigorously vortexed for about 5-10 minutes so that all the lipids sticking in the interior wall get released into the solution. If 96 well-plate is used instead of Eppendorf tube it might lead into trouble by requiring vortexing, which would compromise with the release of lipids from the interior wall of the well. This is why the 96 well plated is considered to be a poor choice. The methanol is expected to dissolve the lipids and make a homogeneous solution. This solution is noted as sample 'B' ('B' for bound to lipids). In the sample B, the MAAs that become bound to lipids are expected to be 100% released in the solution.

Example 6

Absorbance Spectroscopy to Detect Lipid Bound and Unbound with MAAs

A NanoDrop or a Nanophotometer is used to measure the absorbance spectra specific for the MAA, The wavelength ($\lambda_{MAA}$) of the spectrum will be very much MAA specific and every MAA has its corresponding wavelength. For example, $\lambda_{DNA}$=260 nm, $\lambda_{colchicine}$=243 nm, etc. Absorption spectroscopy is performed and the concentration of MAAs in both samples B and UB is quantified. The sample 'UB' stands for unbound with lipids or vesicles) and sample 'B' ('B' for bound to lipids). As the volume of sample UB is 3 times the incubation sample volume, the concentration is adjusted by multiplying the detected concentration from sample UB with 3, From their detected concentrations, the molarities of both lipid bound and lipid unbound MAAs in the incubation tube are calculated. The respective concentrations are $C_{MAA,B}$ and $C_{MAA,UB}$, respectively. The sum of these two concentrations is expected to match with the original MAA concentration ($C_{MAA}$) ensured in the incubation tube during pre-incubation time following the equations:

$$C_{MAA,B}=r_{B,MAA} \cdot C_{MAA}$$

$$C_{MAA,UB}=r_{UB,MAA} \cdot C_{MAA}$$

where $r_{B,MAA}$ and $r_{UB,MAA}$ are the fractions (both are smaller than 1) of liposome bound and unbound MAAs, respectively and they satisfy the following relation:

$$r_{B,MAA}+r_{UB,MAA} \leq 1$$

$$r_{B,MAA}+r_{UB,MAA}=(1-r_{error,detector})(1-r_{loss})$$

Here, $r_{error,detector}$ and $r_{loss}$ are the fractions (both are usually much smaller than 1) of errors contributed due to possible detector's inability to detect 100% (can be referred as instrumental error) and lose of MAAs into the buffer (that can't be detected) due to possible chemical changes, respectively. In ideal cases we may consider:

$$R_{error,detector}=0, \text{ and } r_{loss}=0,$$

or, their possible values can also be calculated from reverse calculations after detecting $r_{B,MAA}$ and $r_{UB,MAA}$.

This DDM helps to quantify liposome binding and unbinding of MAA in an electrical condition that is in a buffer.

The liposome absorbance fraction $A_{B,MAA}$ due to perhaps direct lipid binding is (from reverse calculation after DDM detection of $c_{MAA,B}$ and $C_{MAA,UB}$):

$$c_{MAA,B}/(c_{MAA,B}+c_{MAA,UB})=A_{B,MAA}$$

In ideal cases as mentioned earlier (for $r_{error,detector}=0$, and $r_{loss}=0$) the following relation is valid:

$$A_{B,MAA}=r_{B,MAA}$$

Consequently, the MAA's lipid binding probability ($p_{MAA,lipid}$) is as follows:

$$P_{MAA,lipid}=A_{B,MAA}=r_{B,MAA} \text{ or, } 100 \cdot A_{B,MAA}\%$$

Once the liposome binding fraction is measured, the lipid/MAA mole ratio can be readily quantified using the calculated moles from the total amount of lipids added into the incubation tube.

Example 7

Liposome Binding of Colchicine

Using the previously explained DDM method, the values of $c_{colchicine,B}$ and $c_{colchicine,UB}$ for a series of colchicine concentrations $C_{colchicine}$ was prepared. Up to 2000 μM concentration in buffer solution was measured. FIG. 3 shows the colchicine-Dioleoylphosphatidylcholine (DOPC) liposome assay (DDM) for bound and unbound colchicine using absorbance spectroscopy. DOPC lipid has been used to be consistent with bilayer lipid environment that was used for electrophysiology record.

Example 8

Liposome Binding of Aptamers

FIG. 4 shows the Aptamer liposome assay for bound and unbound aptamer using absorbance spectroscopy. Here for both DPPC and DPPS binding of all three aptamers that were tested using fluorescence have been detected up to equilibrium concentration range. These lipids have been used to be consistent with environments used in MD simulation and fluorescence measurements. Data show 10% binding with PS liposome but negligible binding with PC liposome (data not shown here).

For three derivatives of CD colchicine the ion pore forming concentration in buffer has been observed to be 10-100 μM. For example, the TCC effects are presented in FIG. 1, This is 1000-fold higher than that of AMP Alm concentration in buffer. The detected liposome bound colchicine using DDM is found to be around 1-10 μM corresponding to 10-100 μM concentration in buffer as shown in FIG. 3. That makes a 10% of the colchicine to be absorbed by liposome ($rB_{colchicine}=0.1$). The amount of lipid added into 100 μl was 0.09 mg. This makes 10% of the added colchicine being absorbed by 0.09 mg lipid (~1.145 mM in solution). From this quantitative analysis the bound colchicine/lipid mole ratio in the incubation phase can be measured. This direct mole ratio calculation may appear as a very important quantitative information on target/off-target specific drug binding and thus be helpful in drug discovery.

In case of aptamer-liposome binding detectable fluorescence at around 10-35 μM concentration was observed, while almost identical Aptamer concentrations are detected using DDM as bound to liposome as shown in FIG. 4. This certainly provides a quantitative support in applying DDM as a standard method to detect direct lipid or liposome binding of aptamers. Moreover, this bound Aptamer concentration is found to be 10% of the Aptamer concentration in membrane bathing buffer. That makes 10% of the Aptamers to be absorbed by liposome ($r_{B, Aptamer}=0.1$). The amount of lipid added into 100 μL was 0.1 mg. This makes 10% of the added Aptamers in incubation tube being absorbed by 0.1 mg lipid. From this quantitative analysis we can measure the bound lipid/Aptamer mole ratio in solution. This direct mole ratio may appear as a very important quantitative information on target/off-target specific drug binding and thus be helpful in drug discovery.

One can conclude that the value of the lipid binding probability (pMAA,lipid)≈0.1 for both MAAs colchicine and aptamers is for specific lipid concentrations, as mentioned in above analysis. The change of lipid concentration would perhaps change the whole quantification. This value also is subject to be changed on the relative lipid type change. That makes DDM a general technique to detect membrane association of MAAs.

Example 9

DDM to Address Aspects of Drug Delivery into Cellular Interior Region

Once the value of the lipid binding probability $p_{MAA}$ for the lipid is detected, the fractional intake of the MAAs in the cellular interior region can be determined. In the case of CDs, it is observed that the MAA molecules participate in creating lipid-lined toroidal pores with certain stability. It therefore suggests that after the pore gets destabilized the participating MAA molecules get expelled by the lipid bilayer on it's both surfaces. With an approximation, if we consider that the membrane is symmetric on both sides, which is true in the bilayer membrane constructed for doing electrophysiology experiments as mentioned above, the probability of finding MAA molecules to be expelled by the membrane on its either side is provided by the following expression:

$$P_{MAA,membrane-expelled}=(1/2)(1-r_{MAA,membrane-trapped})p_{MAA,lipid}$$

$r_{MAA, membrane-trapped}$ is a measure of the percentage of lipid bound MAA molecules that gets trapped inside lipid bilayer membrane. The $r_{MAA,membrane-trapped}$ is nothing but the fraction responsible for raising the electrophysiology experimentally measured average value of ion pore activity. That means the higher the value of $r_{MAA, membrane-trapped}$ the larger the membrane-based cytotoxicity to be expected from a specific MAA.

In case of a cell the probability of finding the MAA in the cellular interior region is provided by the following expression:

$$p_{MAA,cell-interior}=p_{MAA,membrane-expelled}=(1/2)(1-r_{MAA,membrane-trapped})p_{MAA,lipid}$$

Here the asymmetry between cellular interior and exterior membrane surface lipid compositions is ignored.

From the above analysis, it becomes clear that DDM therefore provides an approximate measure of the quantitative probability of finding an MAA inside cellular interior region when the MAA approaches to the cell from extracellular hydrophilic environment. DDM therefore may also appear as a powerful tool to help understand the drug delivery phenomena.

The comparable membrane current traces as recorded are presented in FIG. 1. The results clearly suggest that both AMPs and CDs induce conductance events across lipid bilayer membranes. CD induced pores are predicted to be lipid-lined toroidal type with a spontaneously varying constant conductance of the pore in contrast to the protein lined channels reported due to the effects of AMPs gA and Alm where the channel conductance remains unchanged during the lifetime of the specific conductance state of the channels. Despite having varied molecular structures members of both classes of AMPs and CDs are found to induce ion pores/channels across lipid membranes but of course with various types of MAA specific current levels or conductance phenomena. The other class of small DNA oligos 'aptamers' appear as MAAs by showing substantial lipid and aptamer specific liposome binding. All members of these three classes of MAAs namely AMPs, CDs and aptamers are found to be membrane active in different ways. The molecular mechanism behind not only the ion channel formation or liposome binding by MAAs but also general activity of MAAs is desirable. DDM has provided quantitative probability of MAAs' liposome binding.

MD simulations have been performed separately to address the lipid binding of all members from these three mentioned classes of MAAs to understand the molecular level energetics and derive related probability functions.

Example 10

In Silico MD (Molecular Dynamics) Simulation to Detect the MAA Lipid Interaction Energies Using MD, it is possible to track down the energetics between any MAA and any lipid, for example, phosphatidylcholine (PC) or phosphatidylserine (PS). For MAAs, AMPs gA and Alm, CDs TCC and TXL, and aptamers 5'-AAAAGA-3' (Aptamer I) and 5'-AAAGAC-3'(Aptamer II) were used. These comprise the worst (SIAp1) and best (SIAp4) PS containing liposome binding aptamers as illustrated in FIG. 2 among aptamers with short sequences tested for fluorescence measurements. Two different kinds of lipids namely zwitterionic charge neutral PC and negatively charged PS are tested.

Using MD simulation we provide computational support for agent-lipid physical interactions which are postulated to be the mechanisms behind such pore formation. This also sheds new light on the complex interactions between stable structure and liquid crystal structure (e.g., membrane), a very important and still unresolved problem in biophysics and soft condensed matter physics. MD simulations for PS aptamer and CD-lipid have been conducted in our previous works. Using the same settings, similar MD simulations have been carried out for gA- and Alm-lipid pairs.

Three quantities, the separation distance of centers of mass of agent and lipid, $d_{agent\text{-}lipid}$, van der Waals (vdW) and electrostatic (ES) energies were utilized to analyze simulation results. Regarding solvent accessible area (SA), when both drug and lipid molecules are completely separated it is expected for them to be entirely exposed to solvent, i.e., the corresponding SA areas are at a maximum. The SA areas in all studies are roughly unchanged between the start and the investigated 20 Å length. This suggests that within this range the drug lipid complexes stay at an equilibrium solvation condition. Therefore, we will focus only on vdW and ES here.

In order to investigate features of physical interactions of all lipid and agents pairs from MD results, a probabilistic description was considered. Specifically, we first evaluated probability of observing a pair within $d_{agent\text{-}lipid}$ as $P(d_{agent\text{-}lipid})=\Delta t(d_{agent\text{-}lipid})/T_{sim}$, where $\Delta t(d_{agent\text{-}lipid})$ is the time duration the agent-lipid pair stay within $d_{agent\text{-}lipid}$ and $T_{sim}$ is the total simulation time. Second, the probability of having either vdW or ES energy of a lipid and an agent stay at distance $d_a$ gent-lipid is given by Boltzmann distribution:

FIGS. 5A-B shows plots of $P(E(d_{agent\text{-}lipid}))$ against $P(d_{agent\text{-}lipid})$ and the corresponding $d_{agent\text{-}lipid}$ values are represented by symbol size, which is illustrated in the bottom panel. FIG. 5A plots van der Waals energy and FIG. 5B shows the electrostatic energy. FIGS. 5A-B are three dimensional plot showing the case with PC and FIGS. 5C-D shows the case with PS. Furthermore, the FIGS. 5A and 5C shows van der Waals energy and the right FIGS. 5B and 5D show the ES energy. Several features are revealed in this figure. First, it shows similar trends for all three categories of agents against either PC or PS from vdW interactions point of view. Probabilities of having a pair within $d_{agent\text{-}lipid}$ and vdW energy $EvdW(d_{agent\text{-}lipid})$ are gradually decreased when a lipid and an agent separation distance dagent-lipid is increased. Namely, vdW force is likely to play a crucial role in all types of agents to bind with lipids (short dagent-lipid range). Second, however, from ES energy point of view, two CDs are the only type of agents to show similar trends, larger the separation distance dagent-lipid is lower the probabilities P(dagent-lipid) and P(E(dagent-lipid)) are, in both PC and PS cases. It suggests that similar to vdW force, ES force will also likely be a mechanism for the binding process for CDs. Yet, ES force likely to play a minor role in the binding of lipids and agents such as peptides and aptamers. The cause lies perhaps in the polarities of charges on participating agents and thus the ES force can play role either to favor or to disfavor in binding.

One very important message can be drawn from this novel treatment which is if all the important energies plying in the molecular level interactions can be detected then it is possible to correctly predict the binding phenomena. In this regard detection of energies in a single MAA-lipid complex (as done here in our MD simulations) in fact provides better molecular level understanding than in a usually expected MAA-lipid complex in a membrane because this way it is possible to detect the primary (not the collective) energy values. The overall energies in a MAA-lipid complex in a membrane will just be a combination of such many detected energies. Thus the described MD simulation strategy and the detected energy based discovery of the above mentioned two probabilities appear as strong functions correlating the molecular level information with the phenomenological observations of MAA-lipid complexes in lipid membranes as predicted from various in vitro experiments e.g., mentioned a few above. This novel treatment correlates information between in silico and in vitro experiments.

Experimentally, three classes of MAAs AMPs, CDs and aptamers have been reported here to be active in lipid bilayer membranes or liposomes. Both AMPs and CDs are found to be inducing ion pores of different kinds depending on the structure of AMPs and CDs while aptamers are found to be showing direct liposome binding. Despite having different membrane effects MD simulation results suggest that all of these MAAs bind directly with lipids. The mechanisms behind the MD reported lipid binding phenomena have been found to be due to vdW and ES interactions between participating agents. Although the energy scale and polarity of vdW and ES interaction energies are different for different MAAs the underlying mechanisms are always found to be due to charge driven interactions in membrane environment.

This is a very important finding in membrane science because it is demonstrated that various MAAs produce their MAA specific membrane effects based on physical charge interactions between the participating agents.

Based upon the experimental data, a function that would theoretically interpret the energies that have been detected can be developed as universal ones for membrane interactions of MAAs. The geometry and organization of lipids in a membrane make the lipid bilayer an elastic entity with lipid specific curvature profile. Due to the mechanical elastic property and curvature profiles the bilayer can host membrane proteins, ion channels, etc. through geometric/dimensional adjustments. When required the bilayer can deform itself to some extent to hydrophobically couple with membrane hosting structures. gA channels that have been used are shown in FIG. 8, which are shorter than hosting lipid bilayer thickness. In this case bilayer is predicted to deform by decreasing bilayer thickness to hydrophobically couple with the channel. The stability of the hydrophobic gA channel-lipid bilayer coupling requires a general membrane protein (MP) conformational free energy change that is MPs undergo conformational changes reflected in the opening/closing transitions in gA ion channels. It is generally accepted now that in many of the protein conformational changes a perturbation occurs near proteins in the host bilayer incurring an energetic cost $\Delta G_{def}^0$ which contributes to the overall free energy difference $\Delta G_{tot}^{I \to II} = \Delta G_{prot}^{I \to II} + \Delta \Delta G_{def}^{I \to II}$ between two protein states e.g., I and II, where $\Delta G_{prot}^{I \to II}$ is the energetic cost of the protein conformational change per se and $\Delta \Delta G_{def}^{I \to II}$ is the bilayer deformation energy difference between states. In this protein-bilayer interaction, bilayer deformation appears to be a regulator of integral membrane protein functions. To understand this phenomenon, we experimentally and theoretically investigated how lipid membranes with different mechanical, geometrical and electrical properties regulate the integral ion channel energetics using two structurally different gA and Alm channels.

In bilayer-spanning channel formation the association of two trans-bilayer gA monomers is governed by the dimerization coefficient: $K_D = [D]/[M_{gA}]^{-2} = k_1/k_{-1} = \exp\{-(\Delta G_{prot}^0 + \Delta G_{def}^0)/k_B T\}$, where $[M_{gA}]$ and $[D]$ are monomer and dimer concentrations; and $k_1$ and $k_{-1}$ are rate constants determining gA channel appearance rate ($f_{gA} = k_1 \cdot [M_{gA}]^2$) and lifetime ($\tau_{gA} = 1/k_{-1}$)[7]. Here, $k_B$ and T are the Boltzmann constant and absolute temperature, respectively. Since the bilayer deformation energy $\Delta G_{def}^0$ is sensitive to the hydrophobic mismatch ($d_0 - l$) between bilayer thickness ($d_0$) and gA channel length (l), the bilayer responds to its deformation by imposing a restoring/channel-dissociation force $F_{dis}$ on the edges of a channel. Increasing/decreasing $F_{dis}$ is reflected in a decreasing/increasing $\tau_{gA}$ and channels become molecular force transducers. Within limit, the channel structure is invariant when the lipid bilayer thickness is varied, meaning that the gA channels are more rigid than the host bilayer. All-atom molecular dynamics simulations of gA in bilayers[9] show how lipid head groups organize themselves in the region of hydrophobic free length $d_0 - l$. Potential-of-mean-force calculations suggest that trans-membrane protein interactions are regulated by a hydrophobic mismatch equivalent to $d_0 - l$.

The calculation of correct form of $F_{dis}$ has been a long-standing challenge. The comparison between bilayer elasticity based approach and localized charge based approach has been provided in our recent studies and thus the form of $F_{dis}$ has been deducted. Based on the well-appreciated theory of elastic bilayer deformation $\Delta G_{def}^0$ has been found to follow:

$$\Delta G_{def}^0 = H_B \cdot (d_0 - l)^2 + H_X \cdot (d_0 - l) \cdot c_0 + H_c \cdot c_0^2,$$

consequently, $F_{dis}$ to follow:

$$F_{dis} = -(-(\partial/\partial(d_0 - l))\Delta G_{def}^0) = 2H_B(d_0 - l) + H_X \cdot c_0,$$

where $H_B$, $H_X$ and $H_c$ are phenomenological elastic constants.

Using specific 'elastic parameters' in a fluid-like membrane, a good first-order approximation can be created that works well within the limitations of a linear theory. However, in order to extend the applicability of the theory to a nonlinear regime, the screened Coulomb interaction approximation can be used.

The interaction energy between a gA channel and a host bilayer can be calculated based on experimentally observable parameters such as $d_0$, lipid head group cross-sectional area, l, lipid charge $q_L$ and dielectric parameters of the lipid bilayer core, etc. Considering $l < d_0$, the channel extends its Coulomb interaction towards lipids sitting on the bilayer's nearest resting thickness as shown in FIG. 6.

Figure 6:
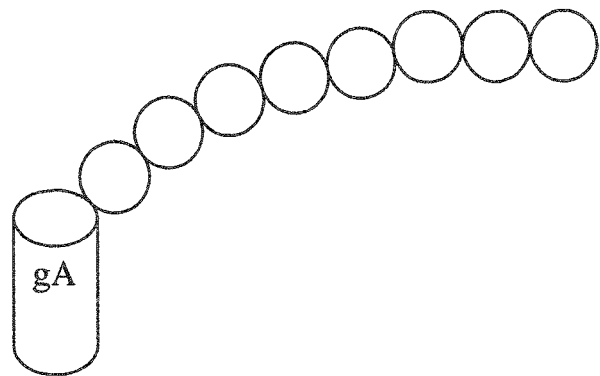
FIG. 6 shows the gramicidin A monomer (gA) in a channel.

As shown in FIG. 6, gramicidin A monomer (gA) in a channel is assumed to find a lipid (just the head group is schematically mentioned) on the perturbed region of the bilayer next to it with bear Coulomb interaction but the next neighboring lipid with first order screened Coulomb interaction and so on. A gA channel directly interacts with a nearest-neighbor lipid by Coulomb forces and this lipid interacts directly with the next-nearest-neighbor lipid but this second lipid's interaction with the channel is screened by the channel's nearest-neighbor lipid. The interaction between the third-nearest neighbor and the channel is screened by the lipids in between. Alternately this mentioned hypothesis can be generalized in the following way. A lipid's head group region may not have any resultant charge, true for zwitterionic lipids. But in the channel lipid complex near the channel the peptide charge polarizes the localized charges in the atomic level in mainly the lipid head group region. The lipid charge $q_L$ can therefore be considered as the resultant of the localized atomic level charges inside any specific lipid under the influence of polarization. The value of $q_L$ therefore is also not constant (though assumed to be constant here for simplicity) for all lipids (e.g., gA's nearest, next nearest, etc.,-neighbor lipids) in the complex as not all lipids fall under identical electric field. This polarization effects of the localized atomic level charges in all atoms in the vicinity of the channel-lipid complex is unavoidable even though either or both of the participating channel/structure inducing agent and lipid may be charge neutral in their independent existence in the hydrophobic lipid membrane. An assumption can be made regarding all lipids participating in this chain that their interactions exist in an identical dielectric environment. In this scenario the general form of the screened Coulomb interaction is provided below:

$$V_{sc}(\vec{r}) = \int d^3k \mathrm{Exp}\{i\vec{k} \cdot \vec{r}\} V_{sc}(\vec{k}) \qquad (1)$$

whose Fourier transform is:

$$V_{sc}(\vec{k}) = \frac{V(\vec{k})}{1 + \frac{V(\vec{k})}{2\pi k_B T} n} \qquad (2)$$

where $V(k)=(1/\epsilon_0\epsilon_r)q_{gA}q_L/k^2$ is the direct Coulomb interaction between gA monomer (charge $g_{gA}$) in a channel and the nearest-neighbor lipid. $k \approx 2\pi/r_{LL}$, $r_{LL}$ is the average lipid-lipid distance, assumed also to be the distance between the channel's longitudinal edge and the nearest lipid head group, n is lipid density ~1/60 Å$^2$. $k_B T \approx 1.38 \times 10^{-23}$ Joule/K (300 K). Here, $\epsilon_0$ is the dielectric constant in vacuum and $\epsilon_r$ (~2) is the relative dielectric constant inside the membrane. When a gA and lipid exist considerably away from each other we can consider both having just one effective charge each as approximated above. But in an MAA-lipid pair or a complex consisting of many MAAs and lipids inside a membrane localized atomic level charges polarize each other and as a result we can consider it a complex of many localized charges where each charge feels screened Coulomb interactions exactly in the manner explained above. In this scenario we define here $V(k)=(1/\epsilon_0 \epsilon_r)q_l q_m/k^2$ with l=m=1, 2, 3, . . . , n and l≠m instead of $V(k)=(1/\epsilon_0\epsilon_r)q_{gA}q_L/k^2$ where $r_{lm}$ is the separation between polarized charges $q_l$ and $q_m$. Here we have considered in a MAA-lipid pair or complex there are altogether n polarized charges that participate in charge based interactions. So instead of considering interactions between an effective charge on MAA and an effective charge on lipid it is more realistic to consider a distribution of charges within the complex and those charges interact with each other following the screened Coulomb interaction formula developed above. Through this consideration the above expression of $\vec{V_{se}(r)}$ becomes a universal interaction potential function for any MAA-lipid complex.

The calculation of energy of a MAA-lipid complex inside a lipid bilayer membrane is described below. For simplicity, we shall consider the calculation of total free energy of a lipid bilayer hosting, e.g., a gA channel relative to the monomer states of gA molecules inside lipid membrane. The binding energy between monomers with identical charge profiles in a gA channel ($U_{g,g}$) is due to the Lennard-Jones and Coulomb potentials which is supported by earlier work on the derivation of an effective attractive interaction potential between charges of the same type (contrary to the generally expected repulsive interaction) in solution. The monomer-monomer binding in a gA channel is comparatively very rigid, which suggest that a change of gA channel stability is mainly due to the change of gA channel bilayer coupling energy ($U_{g,bilayer}$) even though the total binding energy is given by $U(r)=U_{g,g}+U_{g,bilayer}$. Here, $U_{g,bilayer}$ is a $1^{st}$, $2^{nd}$, etc. order term in the expansion of $V_{sc}(r)$ for the hydrophobic mismatch to be filled by single, double etc. lipids representing $1^{st}$, $2^{nd}$, etc. order screening, respectively. Like mentioned earlier for simplicity of calculation, instead of considering a distribution of all polarized charges in the complex created by gA monomers and lipids we have considered here each lipid head group to have an effective polarized charge (which can be a single or combination of a few charges). $\Delta G_{prot}^0$ and $\Delta G_{def}^0$ are proportional to $U_{g,g}$ and $U_{g,bilayer}$ respectively. $F_{dis}$ therefore originates from mechano-electrical properties of membranes although at $d_0-l(\Delta G_{def}^0 \sim 0)$ any fluctuation in $\Delta G_{prot}^0$ may also appear as a channel function regulator.

Recently, using combination of electrophysiology recordings of gA or Alm channel currents in phospholipid bilayer with varied bilayer thickness and numerical computation (NC) on the energies as derived from the above analysis using the channel-lipid screened Coulomb interaction mechanisms we have proven that the bilayer deformation energy changes exponentially with the change of lipid bilayer thickness channel length hydrophobic mismatch $d_0-l$ that is $\Delta G_{I,II} \sim \exp(d_0-l)$. Here I and II are the classical energy states through which the energy transition happens as a result of bilayer deformation near the channel. $\Delta G_{I,II}$ is therefore the measure of the change of the bilayer deformation energy and its value changes as the lipid order changes due to the variation in $d_0-l$. The mentioned hydrophobic mismatch can be varied either by the change of bilayer thickness (as a result of using lipid with varied acyl chain) or change in channel length (as a result of changing gA monomer length). Consequently, $F_{dis} \sim \exp(d_0-l)$ instead of $F_{dis} \sim (d_0-l)$ as derived from the elastic bilayer model calculations which was found apparently not a correct model for the channel energetics.

Figure 9:
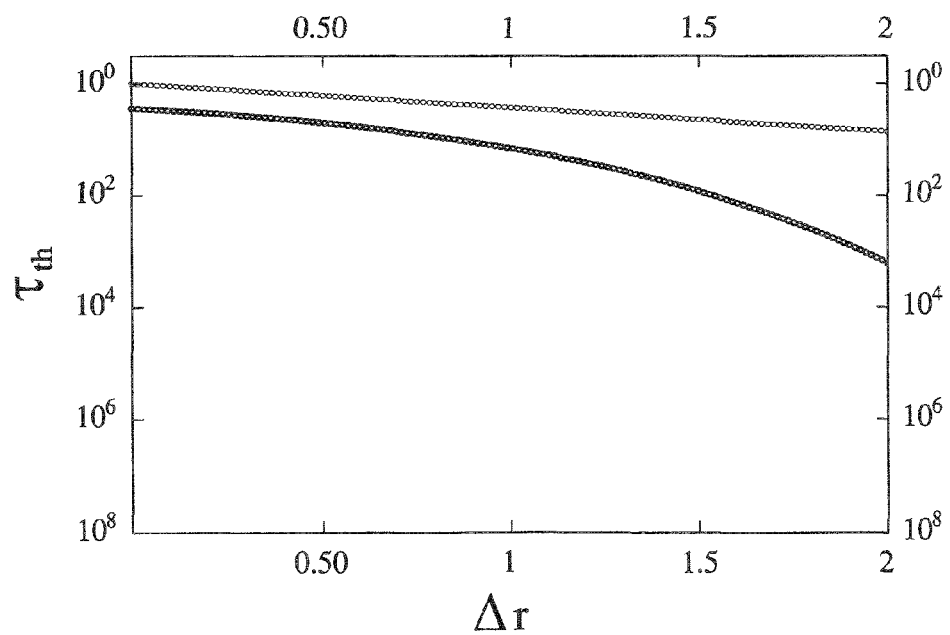
FIG. 9 shows the plot of the theoretical value of gA channel lifetime$\tau_{th}$ (arbitrary unit) versus bilayer thickness gA channel length mismatch $d_{0-l}$ ($\Delta r$, in arbitrary unit).

The channel lifetime follows $\tau \sim \exp\{-\lambda F_{dis}/k_B T\}$ where $\lambda$ is the distance two gA monomers move apart to reach the dimer/monomer transition state. Slight differences in $d_1-l$ dependence of the theoretical trend of gA channel lifetime appear to depend on whether the expression for $F_{dis}$ from the screened Coulomb model (~$\exp(d_0-l)$) is used or the elastic bilayer model (~$(d_0-l)$) assuming $c_0$ to be constant. In both of these cases the theoretical channel destabilization increases (lifetime $\tau_{th}$ decreases) exponentially at small values of $d_0-l$ but as $d_0-l$ increases, higher channel destabilization is observed in the former than in the latter case for example as shown in FIG. 9, which may account for a structural transition in channel structure as is experimentally observed recently.

The exponential energy expression (screened Coulomb model) can be expanded in a power series as follows:

$$\Delta G_{I,II} \sim \exp(d_0-l) \sim \{(d_0-l)^2/2\} + \{1+(d_0-l)+(d_0-l)^3/6+(d_0-l)^4/24+ \ldots\} \sim \Delta G_{I,II}(\text{Harm}) + \Delta G_{I,II}(A.\text{Harm})$$

The harmonic (Harm) and anharmonic (A.Harm) contributions in $\Delta G_{I,II}$ can be observed. The necessity of inclusion of $\Delta G_{I,II}(A.\text{Harm})$ is generally expected in the case with higher values of $d_0-l$ whereas the elastic bilayer theory predicts the presence of only a harmonic term ~$(d_0-l)^2$ in the bilayer deformation energy, which is adequate only for sufficiently small value of $d_0-l$. Importantly, this harmonic term is readily found in our energy $\Delta G_{I,II}$ derived using screened Coulomb interaction function $\vec{V_{se}(r)}$.

Consequently, $F_{dis}=\partial/\partial(d_0-l) \Delta G_{I,II}$ in the screened Coulomb model also contains additional terms (different orders) besides the term ~$(d_0-l)$ which is the only geometric mismatch term found in the elastic bilayer theory to regulate the change of the gA channel lifetime (in the case of non-changing lipid curvature profiles). It can be therefore conclude that although the elastic bilayer model which yields the deformation energy dependence according to ~$(d_0-l)$ may be applicable in the small deformation limit, it requires a modification for values outside this limit. In the case of a higher value of $d_0-l$ the observed destabilization of the channel structure is never energetically understood using a harmonic oscillator type quadratic energy as derived using the elastic bilayer model calculations. This extended calculation of the bilayer gA channel coupling energy based on a standard screened Coulomb interaction adequately explains the exponential damping nature of channel stability and even the structural transition of gA channels as $d_0-l$ increases. It is worth mentioning that in the case of considerable negative values of $d_0-l$ (channel length is greater than bilayer thickness) the screened Coulomb interaction should still play the role of the major interacting component between lipids and the monomers of the channels but since in this case the membrane-channel interaction energy causes a compression of the channels (opposite to pulling apart which happens in the case of positive $d_0-l$), the dissociation of the monomers may also happen as a result of a planar shift and/or bend of the channels. The bending of channels though is a result of the Coulomb interaction. Thus, the charge based interactions again appear as the origin of the mechanical bending. The bending of the channels is however less likely to happen when uniform pulling forces exerted on the channel by the bilayer from both longitudinal edges arise in the case of a positive mismatch. In case of positive 4/elastic bilayer deforms due to a driving force that originates from charge based interaction energies between gA channel and lipids. An ad hoc assumptions on relevant parameters produces $\Delta G_{I,II}$/(kJ/mole) in the low $d_0-l$ limit which is comparable to the literature value. The inventors therefore conclude that the regulation of MP functions is due to the hydrophobic energetic coupling between the bilayer membrane and integral channels as supported by both the model and experimental observations. It can also be concluded that the regulation of MP function may appear as a result of some kind of geometric mismatch adjustment which naturally may appear due to partially the change of the mechanical energetic MP-bilayer coupling but the ultimate origins of all the necessary energies lie in the charge based screened Coulomb interaction energies between participating agents in the complex (as proven from the above treatments). This clearly fall in line with the detected energies namely vdW and ES from our MD results on gA monomer-lipid interactions. Like the source of screened Coulomb interactions both vdW and ES energies originate from the electrical charge based interactions in the complex.

The bilayer regulation of Alm channel energetics is reported to be following the energetics derived from the screened Coulomb Alm-lipid interactions that is almost identical to the gA-lipid interaction energetics.

In CD induced toroidal pore the energetics are found to also follow the identical screened charge interactions. Detailed calculations are not presented here. They are identical to that of channel-lipid screened Coulomb interactions with only quantitative differences. Here charges on CD molecules and lipid head groups in toroidal pore fall within each other's electric fields so a charge based polarization happens and finally all charges interact with others through screened Coulomb interactions as explained earlier.

In Aptamer-liposome binding identical explanations are applicable. That is here too the screened Coulomb interactions are theoretically found (calculations not shown) to be responsible for binding. To have a complete quantitative picture on aptamer-liposome binding energetics, the structure of aptamer-lipid complex in membrane is needed to be considered.

DDM measures the MAA/lipid mole ratio in MAA's liposome binding condition in an aqueous phase. It also measures the lipid binding probability of the MAAs in buffer. That means for a lipid concentration in buffer DDM correctly detects the number percentage of MAAs to be absorbed by liposome. Here the inventors have presented the cases of two classes of MAAs namely ion pore forming colchicine and general liposome binding aptamers that were tested for the liposome absorbance. It was observed $A_{B,colchicine} \approx 0.1$ (here in $A_{B,MAA}$ 'MAA' has been specified as 'colchicine') that is for every 10 colchicine molecules 1 gets absorbed in the liposome constructed by DOPC. For a few aptamers negligible, depending on aptamer type, fraction of aptamers were found to get absorbed by DPPC liposome (data not shown). But as the DPPC liposome was replaced with DPPS liposome it was observed about 5-10% (depending on the aptamer type) of the aptamers to be absorbed by the new liposome. This is consistent with the comparable results as observed in fluorescence measurements on aptamer that were bound to liposomes constructed with DPPC and DPPS at 9:1 mole ratio. This makes the lipid binding probability $p_{MAA,lipid}$ for members of these two MAA classes to be very much specific to the types of both MAAs and liposome containing lipids. The DDM based correct quantification of liposome absorbance of MAAs through lipid specific MAA-lipid binding appears as a novel technique that correctly interprets the origin of MAA effects in membranes which is nothing but perhaps the direct lipid binding of certain fraction of MAAs in the liposome bathing solution.

DDM also helps understand aspects of the drug delivery into cellular interior region which is very important for many drugs that are primarily meant to bind with intracellular targets.

Figure 7:
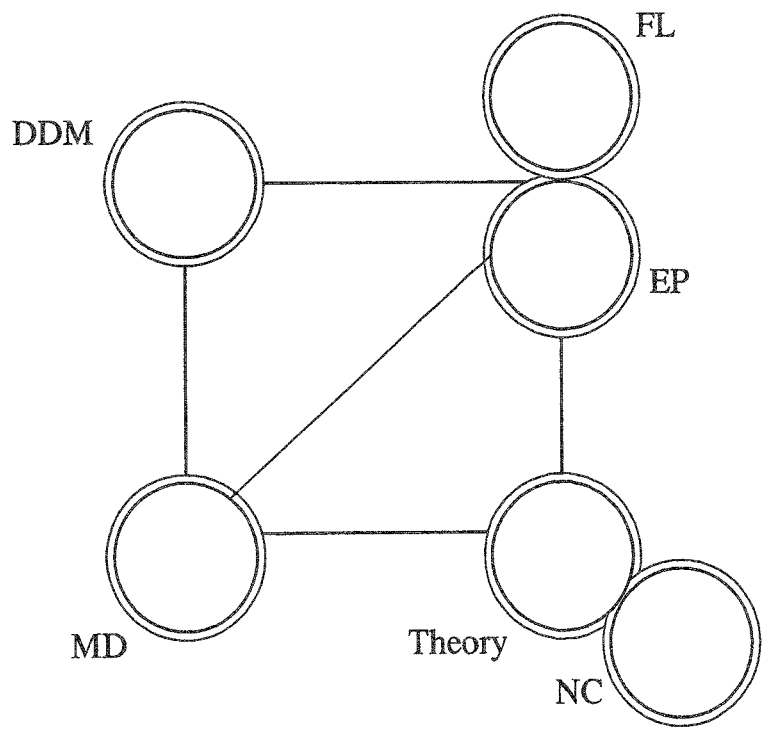
FIG. 7 shows a universal Tetrangle connecting various information on MAA-lipid interactions using various techniques.

The scenario of MD simulation on MAA-lipid complex can be brought to understand the energetics as a result of their mutual association with some order of statistical probability. The mutual association can be ranked from both in silico MD simulation data and in vitro DDM data. MD data additionally can be processed to calculating energetics of the MAA-lipid binding. Considering that the MAA-lipid binding/unbinding happens in a homogeneous environment with equilibrium solvent condition (no hydration effects) so the change of energies are due to only the interaction energies (ES and vdW) that are detected using MD simulations. The exponential of the negative of the change of binding energy in fact provides the measure of the Boltzmann binding probability. Therefore, the distance dependent probability functions as derived using MD data appear as universal functions connecting with lipid binding probability $p_{MAA,lipid}$ detected using DDM for corresponding MAA. The theoretical expression for the binding energies calculated from the screened Coulomb interaction and Lennard-Jones potentials discovers the origins of the energetics to be charge based interactions as detected also from MD simulations. The resultant theoretical driving force as derived using numerical computation (NC) on theoretical binding energies is also found to be nicely fitting in the electrophysiology experimental measurements on stability of the structures as observed as a result of MAA-lipid binding. Taken together all these information from in vitro, in silico and theoretical investigations the following tetrangle (as show in in FIG. 7) is developed to explain the complete features of MAA-lipid binding phenomena. The sides of the tetrangle explain specific features.

There are several potential practical and commercial advantages and applications of the invention. The pharmaceutical companies working to discover novel drugs and drug-delivery techniques will apply our discoveries in the following ways. (i) Drug effects on membrane's lipid target(s) can be understood through measuring true mole numbers of target specific bound MAAs. This will be directly helpful to discover lipid (or in general membrane) targeted drugs. (ii) Detect the lipid binding affinity of drugs that are primarily used to bind with non-membrane cellular targets (e.g., proteins, microtubules, etc.) and thus measure the cytotoxicity of the drugs. This will lead to understanding possible cell death mechanisms through damages in cell membrane regions. This is a very important off-target cytotoxicity aspect for many cell targeted drugs. (iii) The use of DDM can be extended to quantification of lipid binding of nanoparticles to understand their possible membrane trapping mechanisms and as a result membrane based cytotoxicity. It extends our understanding of possible physical lipid interaction based membrane barriers against delivery of nanoparticles into cellular interior regions. (iv) A few energy originated universal probability function has been developed to address the MAA-lipid binding related probabilities that directly correspond to the measured MAA-lipid binding probabilities deducted using DDM. These probability functions provide information on the in silico target binding phenomena of agents where most of the biological parameters are incorporated through programming. These information deducting statistical mechanical methodologies may be utilized by pharma companies working on drug design considering searching for information theory based cheap and alternative techniques. (v) DDM can be used to detect relative intracellular and extracellular drug concentrations and thus quantify the general drug delivery into cellular interior regions where most of the cell based drug target structures responsible for various diseases reside. It is to be mentioned that the cell targeted drugs are generally delivered in the extracellular regions. By detecting the drug concentration in the intracellular cytoplasm relative to the extracellular solution it is possible to obtain a clear picture on cell intake of drugs in its interior region. In cell culture tests the target cells can be treated with different concentrations of drugs for varying time points following which culture supernatants and cell lysates can be collected for determination of the relative drug concentration using DDM.

All of the above mentioned points ((i)-(v)) will be highly considered by pharmaceutical companies while discovering cell targeted drugs and developing cell based drug delivery techniques.

The researchers in academia can use the results and models described herein n the following ways: (vi) The discovered universal tetrangle whose 4 sides connect various technique derived information on MAA-lipid interactions brings the search for novel membrane targeted agents and membrane based cytotoxicity of nonmembrane cell targeted agents on a single platform that provides a complete quantitative and qualitative scientific understanding. This tetrangle will be used by academic researchers to test the potency of any agent to be a membrane active agent and to understand the underlying molecular mechanisms. DDM and all other techniques in the tetrangle will be regularly used in drug discovery research. The tetrangle therefore appears as a universal research platform for researchers engaged in novel molecule inhibitors discovery.

It is to be understood that the present invention is not limited to the embodiments described above, but encompasses any and all embodiments within the scope of the following claims.

We claim:

1. A method for direct detection of lipid binding agents in membrane, comprising the steps of:
   dissolving a lipid in an organic solvent in a container;
   evaporating off the organic solvent to create a lipid film on the inside wall of the container;
   adding a buffer solution;
   adding a known volume of a membrane active agent to the buffer solution;
   incubating the solution in the dark for a period of time;
   removing the buffer solution from the container to provide a solution of sample A;
   washing the container with a buffer solution;
   adding an organic solvent while stirring the container to dissolve the lipid film to create a homogenous solution B;
   measuring the absorbance of the samples A and homogenous solution B by absorption spectroscopy; and
   quantifying the lipid binding energies by the membrane active agents from the absorbance measurements, wherein the membrane active agent is selected from the group consisting of colchicine, aptamer 5'-AAAAGA-3' and 5'-AAAGAC-3.

2. The method for direct detection of lipid binding agents in membrane according to claim 1, wherein the organic solvent is methanol.

3. The method for direct detection of lipid binding agents in membrane according to claim 1, wherein the container is an Eppendorf tube.

4. The method for direct detection of lipid binding agents in membrane according to claim 1, wherein the fixed volume of the organic solvent is about 100 ml.

5. The method for direct detection of lipid binding agents in membrane according to claim 1, wherein the period of incubation time is about one hour.

6. The method for direct detection of lipid binding agents in membrane according to claim 1, wherein the lipid is selected from the group consisting of phosphatidylcholine (PC), phosphatidylserine (PS)) and Dioleoylphosphatidylcholine (DOPC).

7. The method for direct detection of lipid binding agents in membrane according to claim 1, wherein the lipid is a liposome.

8. The method for direct detection of lipid binding agents in membrane according to claim 1, further comprising the step of developing a universal probability function to test and certify an agent as a candidate with measurable probability of interaction or binding with a target structure in a biological system.

9. The method for direct detection of lipid binding agents in membrane according to claim 8, further comprising the step of quantifying a membrane-based cytotoxicity of general drugs.

10. A method for direct detection of lipid binding agents in membrane, the method consisting of the steps of:

dissolving a lipid in an organic solvent in a container;
evaporating off the organic solvent to create a lipid film on the inside wall of the container;
adding a buffer solution;
adding a known volume of a membrane active agent to the buffer solution;
incubating the solution in the dark for a period of time;
removing the buffer solution from the container to provide a solution of sample A;
washing the container with a buffer solution;
adding an organic solvent while stirring the container to dissolve the lipid film to create a homogenous solution B;
measuring the absorbance of the samples A and homogenous solution B by absorption spectroscopy; and
quantifying the lipid binding energies by the membrane active agents from the absorbance measurements, wherein the membrane active agent is selected from the group consisting of colchicine, aptamer 5'-AAAAGA-3' and 5'-AAAGAC-3.

* * * * *

SEQUENCE LISTING

```
<160> NUMBER OF SEQ ID NOS: 2

<210> SEQ ID NO 1
<211> LENGTH: 11
<212> TYPE: DNA
<213> ORGANISM: Artificial Sequence
<220> FEATURE:
<223> OTHER INFORMATION: DNA Aptamer

<400> SEQUENCE: 1
cagaaaaaaa c                                                        11

<210> SEQ ID NO 2
<211> LENGTH: 11
<212> TYPE: DNA
<213> ORGANISM: Artificial Sequence
<220> FEATURE:
<223> OTHER INFORMATION: DNA Aptamer

<400> SEQUENCE: 2
cagaaaaaaa t                                                        11
```